United States Patent [19]

Kroenig

[11] 4,251,555
[45] Feb. 17, 1981

[54] METHOD AND SYSTEM FOR PROCESSING POTATOES

[75] Inventor: Hans E. K. Kroenig, Hilden, Fed. Rep. of Germany

[73] Assignee: Dufrit Kartoffel Verarbeitung Kroenig GmbH & Co. KG, Monheim, Fed. Rep. of Germany

[21] Appl. No.: 13,463

[22] Filed: Feb. 21, 1979

[51] Int. Cl.³ ............................................. G01N 33/02
[52] U.S. Cl. ................................... 426/231; 426/481; 426/518; 209/587; 209/644; 83/404; 83/27; 83/365; 83/411 R; 83/409.2
[58] Field of Search ............... 426/231, 637, 518, 517, 426/481; 209/580, 581, 582, 587, 644; 83/27, 365, 102, 404, 409.2, 411 R; 250/223, 572

[56] References Cited

U.S. PATENT DOCUMENTS

| 3,109,468 | 11/1963 | Lamb et al. | 99/589 |
| 3,382,975 | 5/1968 | Hoover | 209/580 |
| 4,018,674 | 4/1977 | Morris | 209/580 |
| 4,074,808 | 2/1978 | Gillespie | 209/587 |
| 4,147,619 | 4/1979 | Wassmer et al. | 209/587 |

FOREIGN PATENT DOCUMENTS 2621733 12/1977 Fed. Rep. of Germany ........... 209/580

Primary Examiner—S. Leon Bashore
Assistant Examiner—Michael L. Goldman
Attorney, Agent, or Firm—Fitch, Even, Tabin, Flannery & Welsh

[57] ABSTRACT

A method and system are provided for slicing raw, whole potatoes into sticks or strips; sorting the sticks with photoelectric scanners, separating out sticks having black or discolored spots thereon, snipping the ends of the separated sticks and sorting the separated sticks after snipping.

13 Claims, 11 Drawing Figures

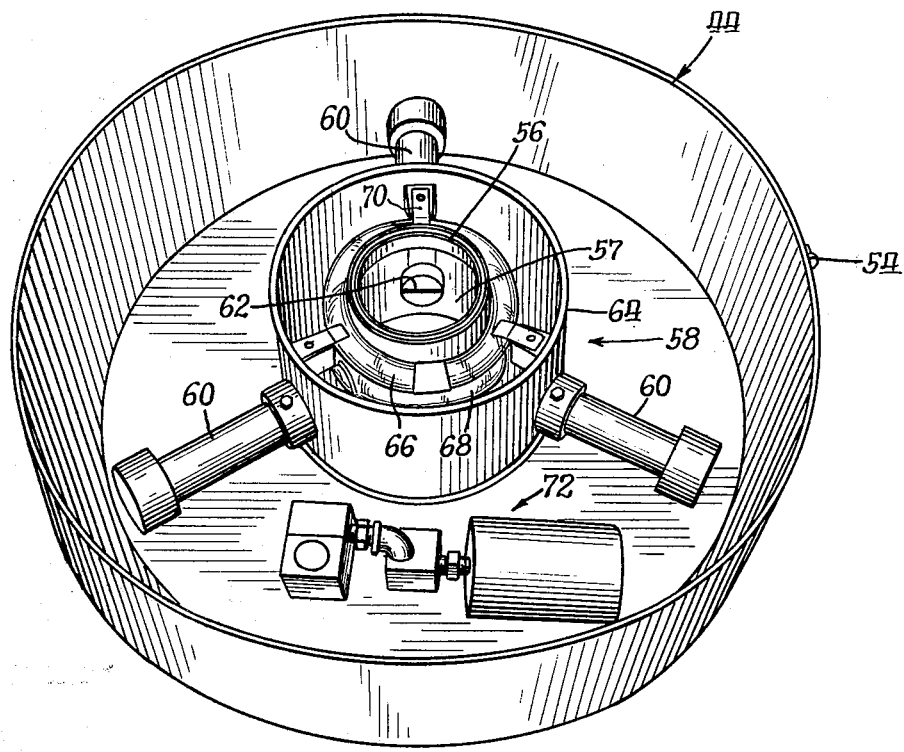
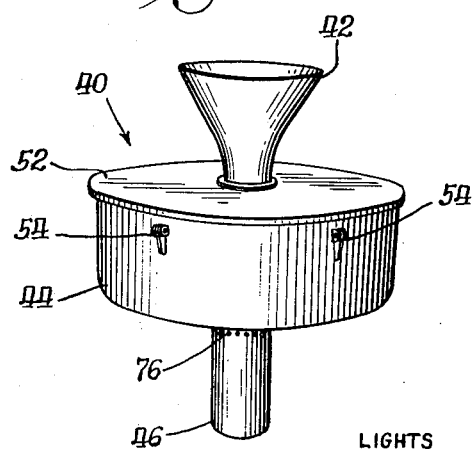
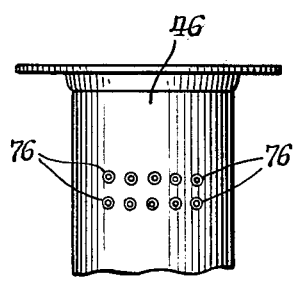
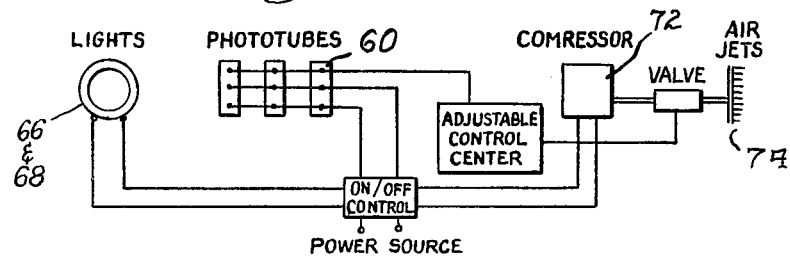

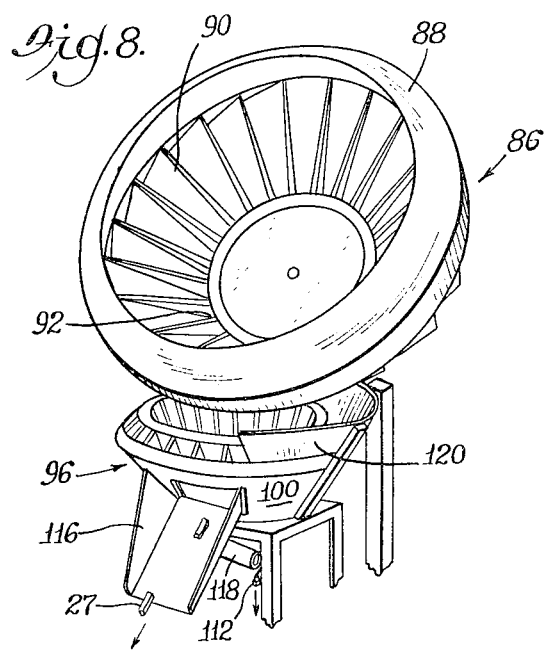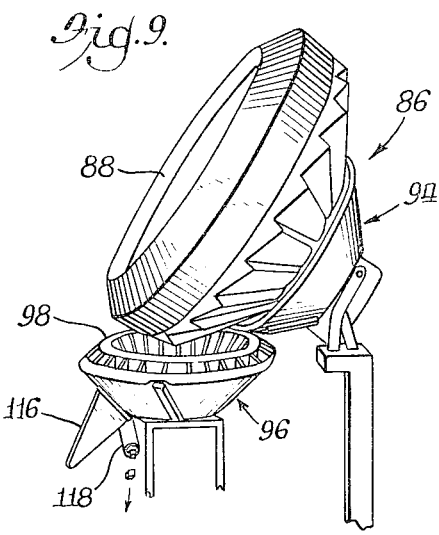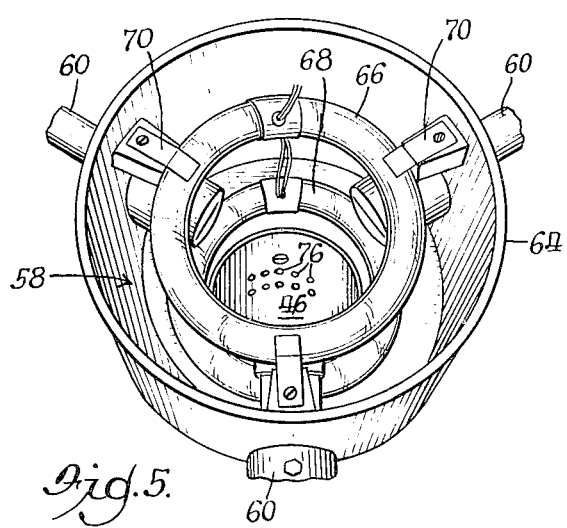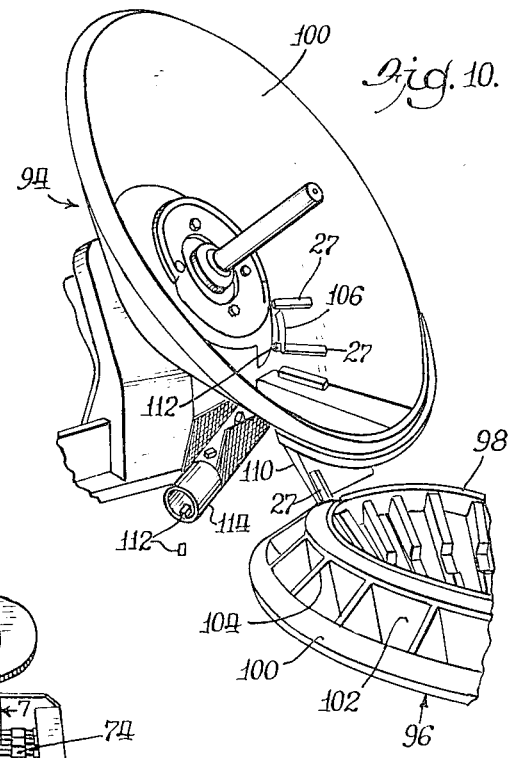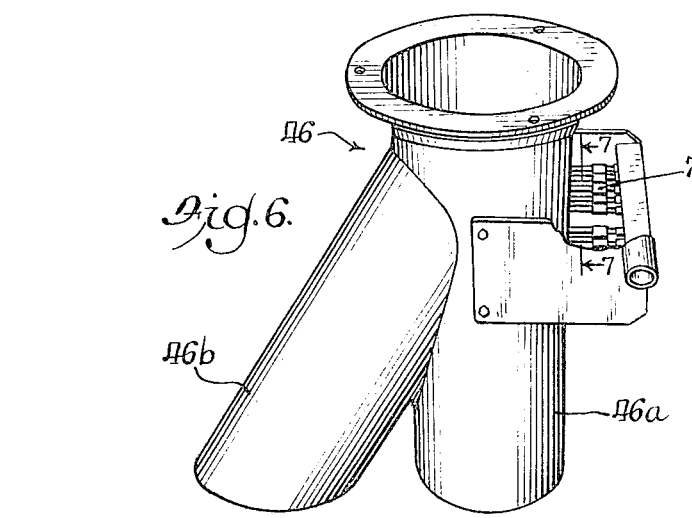

METHOD AND SYSTEM FOR PROCESSING POTATOES

METHOD AND SYSTEM FOR PROCESSING POTATOES

This invention is directed generally to the processing of potatoes in preparation for the production of so-called french fried or string potatoes. More specifically, the invention is directed to a system that cuts raw peeled potatoes into potato sticks and eliminates the black spots and discolored marks that may be present in the sticks.

Potatoes often have bruised spots, eyes, and the like that produce black or discoloration generally on the outside of the potato. When the potatoes are peeled and cut into strips or sticks, these spots are retained on the raw cut sticks which are then passed on for further processing. It is known to carry the raw, whole peeled potatoes in a fluid medium, generally water, and increase the velocity of the medium to force the potatoes through a cross hatching of knives to slice them into generally square cross-sectional strips or sticks. The sticks are thereafter further carried in the fluid medium to a point of further processing. During this process, starch is washed from the outsides of the potatoes and becomes a part of the fluid medium, which starch can thereafter be separated.

It is desirable to sort the potato sticks and separate out the sticks that have black spots or other discoloration. Most generally, these spots are near the ends of the sticks and snipping the ends of the sticks will remove the spots and leave acceptable raw potato sticks. As not all sticks have such spots, it could be wasteful to automatically snip every stick. It is desirable, therefore, to provide a system which can sort out the sticks that need to be snipped. Such is difficult to accomplish while the sticks are carried in a liquid medium, such as water.

Accordingly, it is an object of this invention to provide a system that is extremely rapid and efficient in cutting raw whole potatoes into strips or sticks of predetermined size, sorting the sticks, separating out sticks having black or discolored spots, and snipping the ends of these sticks to remove the spots.

These and other objects and advantages of the invention will become apparent and the invention better understood by reference of the following detailed description read in conjunction with the accompanying drawings in which:

FIG. 3 is a perspective view of a sorting device utilized in the system of FIGS. 1 and 2;

FIG. 4 is a perspective view of the inside of the device of FIG. 3;

FIG. 5 is a fragmented enlargement of a portion of the device shown in FIG. 4;

FIG. 6 is a general side view of the lower portion of the device of FIG. 3;

FIG. 7 is a sectional view of FIG. 6 taken along the line 7—7 thereof;

FIG. 8 is a perspective view of a snipping device utilized in the system of FIGS. 1 and 2;

FIG. 9 is a general side view of the device of FIG. 8;

FIG. 10 is an enlarged perspective view of the device of FIG. 8 with portions removed for clarity of illustration; and FIG. 11 is a schematic diagram of the circuitry generally controlling the sorting device of the invention.

Briefly, raw potatoes that previously have been scraped or steamed peeled by known methods are fed into a supply tank. The tank is kept filled with water or other suitable fluid medium to a predetermined level, and the water is constantly recycled for continuous use. During the time the potatoes are in the hydraulic system, starch is washed from their outer surfaces and is eventually returned to and discharged from this tank.

A food pump is utilized to carry the whole potatoes hydraulically through a feed line to a vegetable slicing apparatus that receives the whole potatoes individually and cuts them into strips or sticks which ultimately are used for the production of french fried or stick potatoes. The resultant sticks at this point represent the maximum length attainable, limited only by the length of the potato being processed. At the same time, the less desirable outside cuts, or the so-called "slabs" that are rounded portions sliced from the outside of the potatoes, are separated from the good center cuts at the vegetable slicing apparatus. It is, of course, important that the slicing is accomplished without damage to the cellular structure of the potatoes.

From the slicing apparatus, the potato sticks are carried in the fluid medium to a position overhead where they are discharged onto a downwardly inclined vibrating screen. After the sticks and fluid separate, the sticks are discharged onto a rapidly moving conveyor where a sorting process in air begins. The purpose of the sorting is to segregate the potato sticks that have black or otherwise discolored spots and send them to a snipping device where their ends are cut off. The sticks are delivered by the fast moving conveyor belt for free-falling through any one of a plurality of sorting devices which include scanners. Any potato stick that has a black or discolored spot is detected by the scanner, which activates air jets to eject such raw potato stick out of its free-falling path and into an alternative path. The non-discolored raw potato sticks free-fall through air through the sorting devices and back into a fluid medium for delivery to a downstream point for further processing.

The ejected raw potato sticks are delivered to a snipping device which cuts a small portion from each end of the raw potato stick, one end at a time. The snipped ends are separated from the raw potato stick which is then returned through the sorting device a second time to assure dark spot removal. Any stick that has a spot remaining is again rejected and sent through the snipping device. The ends are further snipped and the raw potato stick is again delivered back into the system and is scanned again. This process continues until the stick is no longer ejected by the sorters.

Figure 1:
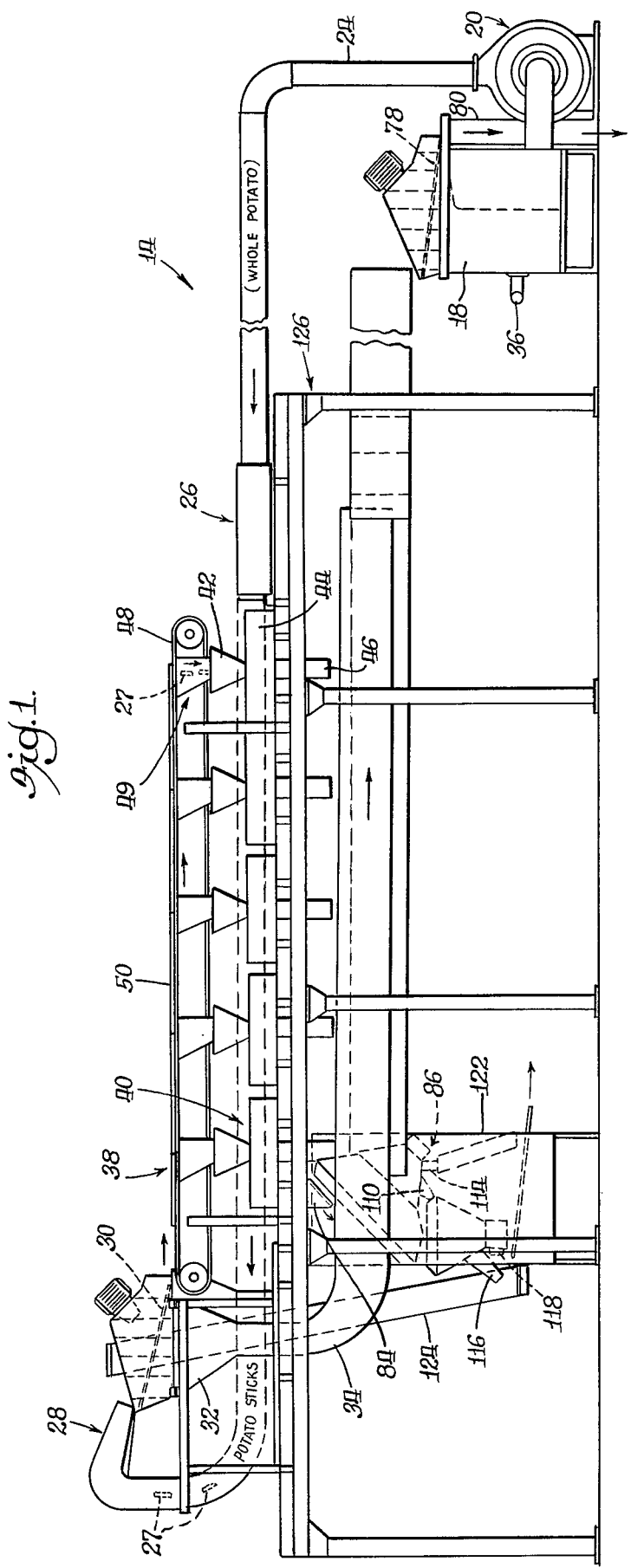
FIG. 1 is a side view in elevation of a system embodying the principles of this invention.
Figure 2:
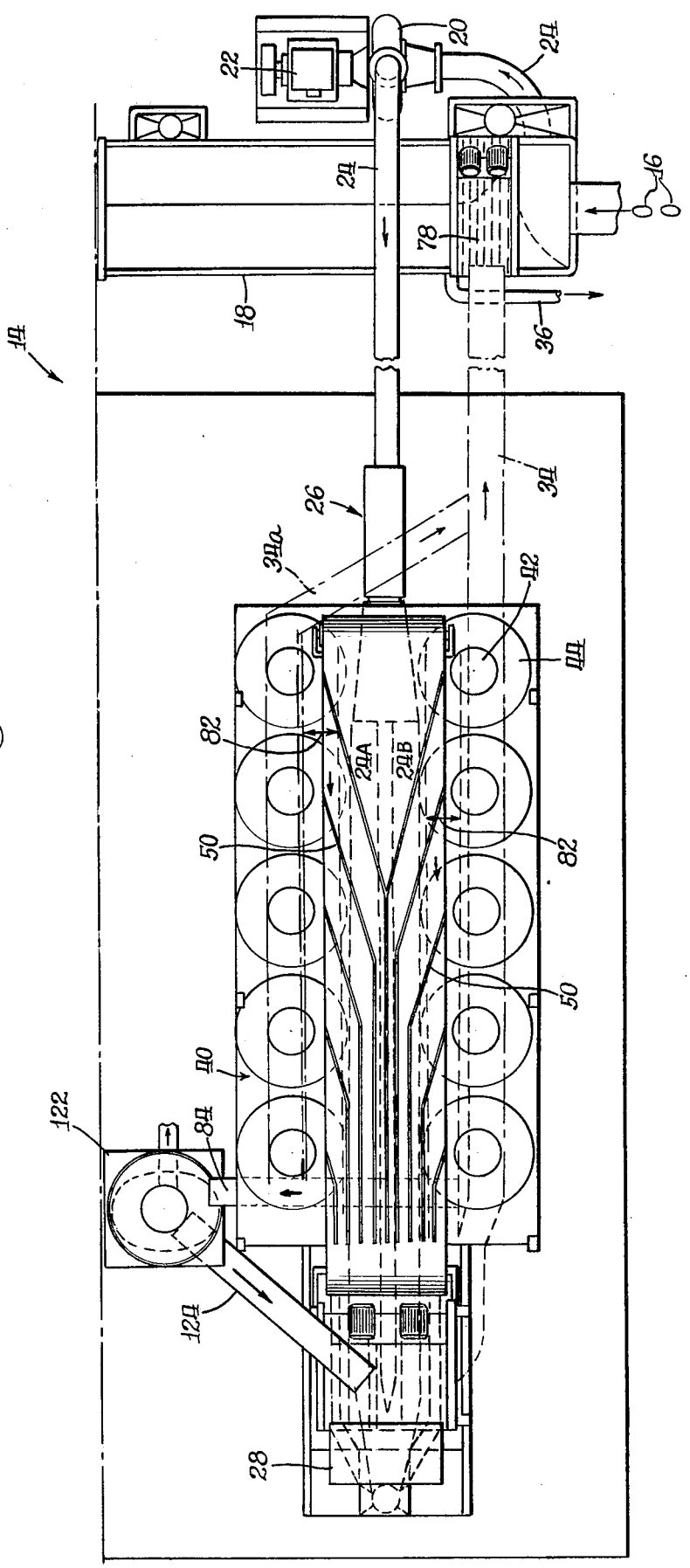
FIG. 2 is a plan view of the system of FIG. 1.

More specifically, and with reference to FIGS. 1 and 2, there is shown a slicing, sorting, and snipping system 14 for the production of raw potato sticks intended for french frying or other uses. Raw whole potatoes 16 (FIG. 2) enter a screened end of a starch removal tank 18. These raw whole potatoes have been previously scraped or steam peeled by known methods. Starch that is carried on the surfaces of the potatoes is constantly being washed from the potato and into the fluid medium, which may be water, at all times it is carried in the fluid. The tank 18 is kept filled with water (or other fluid medium) to a predetermined point, and the water is constantly recycled for continuous use. A food pump 20, driven by a suitable motor 22, carries the raw potatoes hydraulically through a feed line 24 to a vegetable slicing apparatus 26. This apparatus is arranged to center each potato along the longitudinal center of flow so that the potatoes are sequentially fed directly into a cutter mechanism that slices the center of the potato generally into strips or sticks 27 of a square cross-sectional area. The outside slab portions of the potato are separated by a suitable mechanism and discharged to a receiving area (not shown) for further processing. It is important that the slicing operation not damage the cellular structure of the potato. A slicing apparatus that is suitable for this purpose is described in U.S. Pat. No. 3,109,468, issued Nov. 5, 1963, and will not be further described herein.

From the slicing apparatus 26, the raw potato sticks are carried by the fluid medium in the posterior portion of the feed line 24 (FIG. 1) upwardly to a discharge chute 28 where the sticks are discharged onto a downwardly inclined vibrating screen 30. This may be any known type of shaker which would convey the potato sticks to the lower end while permitting the fluid medium to fall through to a receiving funnel 32 which directs the water to a return conduit 34 and back to the tank 18. The water in this way is recirculated through the system except for the starch washed from the potatoes during this processing and which removed through a starch discharge tube 36. The level of the water, of course, must be restored in a suitable manner sufficiently to replenish the effluent of the starch discharge. This may be accomplished in accordance with standard engineering procedures, and the details are not provided here.

At the lower end of the vibrating screen 30, the potato sticks are discharged onto a conveyor 38, which carries the sticks away from the point of discharge and overhead of the feed line 24. As can be seen in FIG. 2, this feed line 24 may be split into two separate conduits 24a and 24b to increase the volume of the conduit and thus reduce the velocity of the transporting fluid. The velocity of the fluid on the input to the slicing mechanism 26 is utilized to carry each potato through the slicing mechanism, and such a velocity is not required on the output side of the slicer for carrying the potato sticks to the discharge chute 28. The conduits 24a and 24b, however, extend underneath the conveyor 38 and in between two rows of inverted conelike devices or sorters 40, which also are underneath the conveyor 38. In the illustrated embodiment, ten such sorters are shown, five on either side of the conduits 24a, b. From the external appearance, the sorters 40 include an inverted cone 42 top portion, a relatively large round circular body 44 portion, and a discharge tube 46 lower portion.

The conveyor 38 includes a belt 48 that runs at high speed and a plurality of dividers 50 that deflect the raw potato sticks as they are carried on the high speed belt 48 into a plurality of separate paths 51 adjacent the dividers and distribute them to the various sorters. There is a divider 50 to deflect sticks to each of the illustrated sorters 40, the dividers acting as cams directing the sticks to separate points on the side edges of the conveyor belt 48 just overhead of the sorters. Each inverted cone 42 acts as a funnel to receive the sticks as they fall off the edge of the conveyor belt 48 as illustrated at 49. It will be noted that this is a free fall in air of the raw potato sticks, the other fluid having been removed as the sticks traversed the vibrating screen 30. Each falling potato stick is directed by the inverted cone 42 toward the center of the device where it continues its free fall through the body 44 and into the discharge tube 46.

For a description of the operation of the sorter 40, reference is now made to FIGS. 3-7. An external view of sorter 40 is shown in FIG. 3, wherein the circular body 44 is seen in its cylindrical form with a removable top 52 closing the upper end of the body. Hinged clamps 54 are provided on the body to retain the top 52 in position. The clamps are shown in the open condition, wherein the top 52 is removable. Preferably, the sorter 40 is made of stainless steel.

FIG. 4 is an interval view of the sorter 40 after the top 52 has been removed. Exposed, is a concentrically located, double-walled tube 56. The tube must readily pass light, therefore, the material should be clear and colorless. A product of synthetic resin materials sold under the tradmark PLEXIGLAS is a suitable material for the tube. The raw potato sticks free fall through the tube 56, and the purpose of the double wall is to eliminate condensation which might otherwise occur from the combination of the moisture still carried by the sticks and the heat generated by the internal components of the sorter 40. The tube 56 defines a chamber 57. The raw potato sticks free-fall axially through the air through the chamber 57.

Surrounding the double-walled tube 56 is a scanner 58, which is responsible for the ejection of raw potato sticks having black or discolored spots. This scanner 58 includes three phototubes 60. These three phototubes are located in the same plane and circumferentially around the tube 56 approximately 120° apart from each other. A slit 62 is visible on the front end of one of the phototubes, and this slit is utilized in the aiming of the tubes, which are all directed toward the chamber 57. Located in this fashion, the three phototubes 60 scan a ring in their plane in the chamber 57 that is approximately three quarters of an inch thick. The raw potato sticks pass through this ring transversely during their free-fall.

A support cylinder 64 provides structure for supporting the three phototubes 60. In addition, at least one high intensity fluorescent light 66 surrounds the tube 56. In the illustrated embodiment, two such high intensity fluorescent lights 66 and 68 are provided, one above the plane of the phototubes and the other below as best seen in FIG. 5. These illuminate the chamber with a constant intensity. Both fluorescent lights are ring-shaped and are supported by suitable brackets 70. The inside surface of the cylinder 64 is coated with a suitable light, highly reflective material. Returning to FIG. 4, an air compressor 72 is also provided within the body 44 adjacent the scanner 58. This air compressor 72 powers a plurality of air jets 74 that are mounted on the lower discharge tube 46 of the sorter 40. These air jets are best seen in FIG. 6. A corresponding number of ports 76 (FIG. 7) are provided in the discharge tube 46 to receive the air jets 74. The relationship of these ports and air jets to the scanner 58 is best seen in FIG. 5. Thus the air jets are located a short distance below the scanner 58. The compressor 72 includes appropriate valves, tubes, electric power lines from a source, and electrical controls to complete its operation. These are not shown in order to simplify the illustration. The connections are all made in accordance with standard engineering principles. Likewise, the electrical circuitry for the phototubes and fluorescent bulbs is not shown in its complete form, as these, too, are connected according to standard electrical engineering principles. A schematic of this control circuitry is shown in FIG. 11.

The phototubes 60 may be conventional photosensitive or light-actuated electron tubes, often popularly known as electric eyes. Basically, these tubes consist of a cathode which is photo emissive and an anode for collecting the electrons emitted by the cathode. The scanner analyzes the light values of the subject raw potato sticks as they fall through the ring scanned by the phototubes. The subject sticks are illuminated by the high intensity light source of constant intensity. The phototubes aimed in this area receive transmitted or reflected light from the subjects and provide a signal output proportional to the subject brightness as required. An adjustable electronic control is provided for each scanner as indicated in FIG. 11. Adjustments can be made to control the amount of opacity in the raw potato stick needed to require rejection. Further, this electronic control can adjust the amount of air used for rejection, and the length of time between scanning and the release of air. There may be a few milliseconds delay between the time of detecting a stick having a dark or discolored spot and the command of the scanner signal to release the air that will divert the potato stick at the appropriate time in its fall. Referring once again to FIG. 6, shown there is the lower discharge tube 46 which fits below the body 44 of the sorter 40. It will be seen that the discharge tube 46 divides into two paths or branch tubes 46a and 46b. The multiple air jets 74 are located just opposite the juncture of the branches 46a and 46b. The good raw potato sticks fall directly through the system in the path of the branch 46a. A raw potato stick that includes a black or discolored area is detected by the scanner 58 and, upon command, the air jets 74 timely blast the stick out of the falling path 46a and into the path of the branch tube 46b.

The scanner 58 of the illustrated embodiment is capable of 750 sightings per minute. The combination of the ten scanners and the conveyor operate to sort approximately 7 to 9 tons of cut raw potato sticks per hour.

Returning once again to FIG. 1, it has been mentioned that the good raw potato sticks fall directly through the path 46a of the discharge tube 46 at the lower part of the sorter 40. These good sticks fall directly into the return conduit 34 which is carrying the fluid separated from the potato sticks at the head end of the system at the vibrating screen 30. The sticks fall into this returning fluid and are carried thereby to a second downwardly inclined vibrating screen 78 located over a portion of the tank 18. As can be seen in FIG. 2, a branch 34a catches the sticks from one row of the sorters 40 and feed them into the conduit 34 for delivery to the vibrating screen 78. Again, the raw potato sticks traverse downwardly to the end of the screen while the fluid falls through the screen to the tank below. As the raw potato sticks reach the discharge end of the screen 78, they free-fall through a receiving tube 80 which delivers the raw potato sticks away from this system and into further processing or packaging.

The raw potato sticks that are ejected by the sorters 40 fall through the path 46b onto conveyors 82 or other suitable transporting means which carry the sticks in a reverse direction in the system (back toward the left in FIGS. 1 and 2) to a discharge chute 84, which in turn drops the sticks into a potato snipping device 86, best seen in FIG. 1.

Very generally, in this potato snipping device 86, one end at a time of each potato stick directed thereto has from one quarter to one-half inch cut and separated from the stick. This is accomplished by the potato stick falling first into one cutting device which snips one end, and then by gravity and centrifugal force, falls into a second cutting device which cuts the other end. The cut ends may then be directed to an offal outlet or to other processing as desired, and the main body of the stick is returned to again pass through the scanners.

For a description of the snipping device 86, please refer to FIGS. 8 through 10. A large stainless steel ribbed cowl 88 is mounted to rotate and has an open end facing upwardly to receive the falling ejected raw potato sticks from the discharge chute 84 (FIG. 1). Preferably, a spray of water is applied to assist the movement of the potato sticks downwardly in the rotating cowl. A series of parallel ribs 90 line the inside wall of the cowl, and the potatoes fall between the ribs and are directed downwardly into openings 92 between the ribs.

From the side view in FIG. 9, it will be seen that the snipping device 86 actually includes two separate cutting devices. The cowl 88 is removable, and when it is removed, two cutting devices 94 and 96, which may be identical, are exposed. The cutter 94 is located above and at approximately a 45° angle to the lower cutter 96. With reference now to the lower cutter 96 in FIG. 10, these cutting devices 94 and 96 each comprise an inner, fluted rotating bowl 98 and an outer stationary bowl 100. Between these two bowls are a series of side by side chambers 102 defined on two sides by the walls of the two bowls and on the other two sides by a plurality of spaced side walls 104 attached to the outer wall of the inner rotating bowl 98 and extending at approximately a 90° angle to the wall of the bowl. Consequently, the side walls 104, and consequently the chambers 102, rotate with the bowl 98 while the outer bowl 100 remains stationary. The upper cutting device 94 in FIG. 10 is shown with the rotating bowl 98 removed, leaving the stationary bowl 100 exposed to view.

Referring once again to FIGS. 8 and 9 the cowl 88 is fastened in a suitable manner to the rotating bowl 98 of the upper cutting device 94. The openings 92 between the ribs of the cowl align with the chambers 102 between the bowls. Consequently, the sticks slide down the cowl between the ribs and into the chambers 102 of the upper cutting device 94. The potato sticks fall lengthwise into these chambers and downwardly to the bottom of the chamber. By that time the side walls 104 of the chamber have carried the sticks to the lead edge of a cutting knife 106. This cutting knife is seen in FIG. 10 with a potato stick 27 about to reach the lead end of the knife 106, another potato stick 27 passing over the cutting knife 106, and yet another potato stick 27 already cut and ready to fall into a delivery chute 110. The delivery chute 110 aligns with the chambers 102 of the lower cutting device 96. As the rotating bowl 98 causes the side walls 104 to move past the chute 110, the falling potato sticks 27 are dropped into the chambers 102, as illustrated by a potato stick 27 shown presently on the chute 110. Snipped ends 112 are shown on the opposite side of the knife blade and are directed into an end chute 114 for further delivery either to a catch can or other device for delivery to further processing or to an offal outlet, as suitable. The knife 106 is located a spaced distance from the bottom equal to the desired length of end to be cut from the potato stick. Generally, this desired length will be between one-quarter inch and one-half inch, although some other length may also be suitable.

Following the progress of the potato sticks 108 exposed in the cutting bowl 100 of the upper cutting device 94 in FIG. 10, it will be seen that the non-snipped end of a potato stick from the upper cutting device 94 is directed downwardly and becomes the lead end as it falls into a chamber 102 of the lower cutting device 96. It is this lead end of the stick that is cut by the knife blade 106 of the lower cutting device 96.

Returning attention to FIG. 8, the potato stick 27 now having both of its ends cut off is discharged in a final chute 116 while the snipped ends are separately discharged in a final end chute 118. Also, it will be seen that a deflector 120 is provided around a portion of the circumference of the stationary bowl 100 of the lower cutting device 96 to be certain that the potato sticks passing from the upper to the lower cutter are not knocked over the side by a moving part of the rotating bowl 98.

Referring once again to FIG. 1, the entire snipping device 86 is contained generally within an enclosure 122 located below both the conveyor 38 and the line of sorters 40. As the potato sticks are discharged from the final chute 116, they fall onto a return conveyor 124 which elevates them back to an overhead position for discharge once again into the system at the vibrating screen 30 where they join sticks being separated from the fluid medium. Thus, the sticks again pass through the sorting system along with those passing through for the first time. Once again, if the snipped ends have not removed the black or discolored spots from the stick, the scanners will eject the stick for a return pass through the snipping device 86 as just described. It again is returned via the return conveyor 124 for another pass through a scanner. This process will repeat until the dark spot has been removed and the stick is accepted by the scanner to fall directly into the return conduit 34 and thence to the vibrating screen 78 and receiving tube 80 for further processing. The more a given stick is snipped, of course, the shorter it becomes. As mentioned earlier, however, most spots are on the outer surfaces of the whole potatoes, and so generally a first pass through the snipping device 86 of the sticks having black or discolored spots will remove the spots.

The entire system as described is supported on a main structure 126. It should be understood, that while a single structure has been shown to support two rows of five each sorters and an overhead conveyor 38 along with a snipping device 86, the system could be expanded to include more of these devices. For example, a second such structure might parallel the structure just described and use the snipping device 86 in common to thereby double the output of the system. There is no intention of limiting the system to the quantity of devices shown, as they have been selected for purposes of illustration and description only.

Thus, there has been provided in accordance with this invention a system that interfaces means for the slicing of raw peeled potatoes into sticks with means for sorting and separating out the raw potato sticks that have black or discolored spots thereon. Such spots are generally near the ends of the sticks (the outside surface of the potato) and the system includes means for snipping the discolored ends to provide a clear raw potato stick. The system recycles all snipped raw potato sticks for further sorting to assure complete black spot removal. The accepted raw potato sticks are made available for further processing.

While the invention has been described in connection with a preferred embodiment, alternatives, modifications, and variations may be apparent to those skilled in the art in view of the foregoing description. Accordingly, it is intended to embrace all such alternatives, modifications and variations as fall within the spirit and scope of the appended claims.

What is claimed is:

1. A method of sorting raw potato sticks to separate out those having black or discolored spots thereon and snipping the ends of the separated sticks to remove the spots, comprising the steps of providing individual raw sticks in a liquid medium in a liquid transporting means from a source, separating the sticks from the liquid medium, sorting the sticks in air by dividing the separated sticks as they are conveyed on a conveyor belt into a plurality of paths that terminate at separate points along the side edges of the conveyor belt, dropping the sticks individually from the conveyor belt at the end of each path for free-fall through a photoelectric scanner located therebelow, detecting each stick having a dark or discolored spot, providing a signal corresponding to each such detection, ejecting each such detected stick during free-fall thereof to an alternative path in response to said signal, snipping the ends of the ejected sticks, and transporting all sticks not ejected away for further processing or packaging.

2. A method in accordance with claim 1 further comprising the steps of repeating the sorting, ejecting and snipping steps for each stick having its ends snipped until the black or discolored spots are removed from the sticks.

3. A method in accordance with claim 1 wherein the step of separating the sticks from the liquid medium includes passing the sticks over a vibrating screen and onto the conveyor belt.

4. A method in accordance with claim 1 wherein the snipping of the sticks includes the steps of receiving the ejected sticks in a first cutting chamber, cutting one end of each stick, transferring each stick to a second cutting chamber, cutting the other end of the stick in the second chamber and separating the cut ends from the sticks.

5. A method for slicing raw whole potatoes into sticks, sorting the sticks to separate out those having black or discolored spots thereon and snipping the ends of the separated sticks to remove the spots, comprising the steps of providing peeled whole raw potatoes in a liquid medium, forcing the potatoes through a network of knives to produce individual raw elongated sticks, separating the sticks from the liquid medium, sorting the sticks in air by dividing the separated sticks as they are conveyed on a conveyor belt into a plurality of paths that terminate at separate points along the side edges of the conveyor belt, dropping the sticks individually from the conveyor belt at the end of each path for free-fall through a photoelectric scanner located therebelow, separating out sticks having black or discolored spots by detecting such sticks during free-fall through each scanner, providing a signal corresponding to each such detection, ejecting each such detected stick during free-fall thereof out of the free-falling path to an alternative path in response to said signal, snipping the ends of the separated sticks having spots, and transporting all sticks without black or discolored spots away for further processing or packaging.

6. A system for sorting raw potato sticks to separate those having black or discolored spots thereon and snipping the ends of the separated sticks to remove the spots, comprising: means for conducting the raw stick in a liquid medium from a source; means for separating said sticks from the liquid medium; means for sorting the sticks while moving in air, said sorting means including conveyor means having a plurality of stationary dividers thereover that divide the sticks into a plurality of separate paths as the sticks are conveyed, the paths terminating at separate points along the side edges of the conveyor means; photoelectric scanner means located below each path end for receiving the sticks in free-fall therethrough and detecting those sticks having black or discolored spots thereon; means for separating out sticks having black or discolored spots thereon during free-fall in response to said scanner means; means for snipping the ends of the separated sticks having spots; and means for transporting all sticks without black or discolored spots away for further processing or packaging.

7. A system in accordance with claim 6 further comprising means for returning each separated stick having spots to the sorting means after snipping.

8. A system in accordance with claim 6 wherein said means for separating the sticks from the liquid medium includes a downwardly inclined vibrating screen and wherein said conveyor means is a belt located adjacent said vibrating screen.

9. A system in accordance with claim 6 wherein said scanner means includes a double-walled cylindrical tube of clear material defining a chamber through which the sticks are permitted to free-fall; at least one ring-shaped high-intensity light surrounding said cylindrical tube and illuminating said chamber with a constant intensity; a plurality of phototubes located in a common plane and circumferentially displaced from each other around said tube and aimed toward said chamber; and an electrical operating circuit connecting said phototubes and providing a signal in response to predetermined opacity of the sticks as they fall through the chamber.

10. A system in accordance with claim 9 wherein said means for ejecting the sticks having black or discolored spots includes an air compressor and a plurality of air jets connected thereto controlled by the signal of said scanner means, said air jets being located below said chamber and providing a force of air transversely of the path of the free-falling sticks upon command of said scanner that is capable of diverting a free-falling stick out of its path.

11. A system in accordance with claim 10 further comprising means for adjusting the timing between detecting a stick of a predetermined opacity and the energizing of the air jets to eject that stick out of its free-falling path and means for adjusting the point of opacity of the sticks at which the signal will be provided for energizing the air jets.

12. A system for slicing raw whole potatoes into sticks, sorting the sticks to separate out those having black or discolored spots thereon and snipping the ends of the separated sticks to remove the spots, comprising: means for conducting the whole potatoes in a liquid medium to slicing apparatus; slicing apparatus receiving the whole raw potatoes and slicing them individually into elongated raw sticks; means for separating said sticks from the liquid medium carrying the sticks; means for sorting the sticks while moving in air, said sorting means including conveyor means having a plurality of stationary dividers thereover that divide the sticks into a plurality of separate paths as the sticks are conveyed, the paths terminating at separate points along the side edges of the conveyor means; photoelectric scanner means located below each path end for receiving the sticks in free-fall therethrough and detecting those sticks having black or discolored spots thereon; means for separating out sticks having black or discolored spots thereon during free-fall in response to said scanner means; means for snipping the ends of the separated sticks having spots; and means for transporting all sticks without black or discolored spots away for further processing or packaging.

13. A system in accordance with claim 12 further comprising means for returning each separated stick having spots to the sorting means after snipping.

* * * * *